United States Patent
Ragsdale

(10) Patent No.: US 8,221,299 B2
(45) Date of Patent: Jul. 17, 2012

(54) CENTRIFUGAL FORCE-BASED SYSTEM FOR DETECTION/TREATMENT OF MEMBRANE-ENCASED STRUCTURES

(75) Inventor: Charles W. Ragsdale, Concord, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 410 days.

(21) Appl. No.: 12/477,701

(22) Filed: Jun. 3, 2009

(65) Prior Publication Data

US 2010/0041122 A1 Feb. 18, 2010

Related U.S. Application Data

(60) Provisional application No. 61/073,135, filed on Jun. 17, 2008.

(51) Int. Cl.
*B04B 15/00* (2006.01)
(52) U.S. Cl. .............. 494/10; 435/286.5; 435/287.1; 435/288.7; 494/4; 427/2.11; 427/10
(58) Field of Classification Search .............. None
See application file for complete search history.

(56) References Cited

U.S. PATENT DOCUMENTS

| | | | |
|---|---|---|---|
| 2002/0088712 A1* | 7/2002 | Miles | 204/547 |
| 2003/0232403 A1 | 12/2003 | Kellogg et al. | |
| 2004/0234970 A1* | 11/2004 | Yoo | 435/6 |
| 2005/0014249 A1 | 1/2005 | Staimer et al. | |
| 2005/0037484 A1* | 2/2005 | Staimer et al. | 435/287.2 |
| 2007/0267361 A1 | 11/2007 | Tyvoll et al. | |
| 2010/0041562 A1* | 2/2010 | Li et al. | 506/9 |

OTHER PUBLICATIONS

Huh, Dongeun et al.; "Microfluidics for flow cytometric analysis of cells and particles"; 2005, *Physiol. Meas.*, vol. 26, pp. R73-R98.

* cited by examiner

*Primary Examiner* — N.C. Yang
(74) *Attorney, Agent, or Firm* — Kilpatrick Townsend & Stockton LLP.; M. Henry Heines

(57) ABSTRACT

Membrane-encased structures such as biological cells, liposomes, and vesicles, are conveyed through one or more channels in a rotating disk for individual exposure to optical elements or to electrodes, for purposes of transfection or flow cytometry. The rotation of the disk serves either to provide centrifugal force to urge the cells against one wall of the channel and in certain embodiments to move the cells through the channels, or to draw cells at preselected times or intervals into the exposure zone, or all three.

12 Claims, 3 Drawing Sheets

CENTRIFUGAL FORCE-BASED SYSTEM FOR DETECTION/TREATMENT OF MEMBRANE-ENCASED STRUCTURES

CROSS-REFERENCE TO RELATED APPLICATION

This application claims the benefit of U.S. Provisional Patent Application No. 61/073,135, filed Jun. 17, 2008, the contents of which are incorporated herein by reference.

BACKGROUND OF THE INVENTION

1. Field of the Invention

This invention lies in the field of manipulations of biological cells, and particularly methods for causing cells from a cell suspension to flow past a detection or treatment site in a single file or at a controlled rate.

2. Description of the Prior Art

Systems for detecting, analyzing, or transforming biological cells or other membrane-encased structures such as liposomes or vesicles are most often designed for batchwise operation. Transfection, for example, is typically performed in batchwise manner in a cuvette. Batchwise transfection involves manipulation of the cells and system components and repetitive processing steps, either by a laboratory technician or an instrument, and the quantity of cells or other structures that are transfected, as well as the rate at which the cells are processed, are subject to the size limitations of the typical cuvette. For these reasons, the processing of large volumes of sample and large numbers of structures is costly and prone to error. In procedures in which transfection is performed by electroporation, the repeated use of an electroporation chamber can cause overheating of the chamber, and the use of an overheated chamber can cause irreparable rupture of the cell membranes. Continuous-flow systems for electroporation have been contemplated but very little, if any, successful design work has occurred. The detection and characterization of cells by continuous flow, on the other hand, are commonly performed by flow cytometry. Although it is a well-known procedure, flow cytometry involves the use of costly fluidics components and the small channels through which the cells pass in flow cytometry instruments are susceptible to clogging.

SUMMARY OF THE INVENTION

The present invention uses a rotating disk for conveying biological cells and comparable structures through a passage in a single-file manner without the need for complex conveyance mechanisms and yet with minimal or no loss of flow control. The passage is a channel, either open as a trough or closed as a tunnel, that runs through the disk and defines a path of travel whose radial distance from the center of the disk continuously increases through the channel. The passage terminates in an outlet port that is either at the outer edge of the disk or adjacent to the outer edge, and the rotation of the disk is in a direction that promotes the movement of the cells through the passage toward the outlet port. Thus, when the passage is shaped as a spiral, for example, the direction of rotation is such that the passage spirals outward rather than inward.

The systems of this invention are useful for cell transformations such as electroporation and laser-induced poration as well as for cell measurements, including optical measurements, such as those performed in conventional flow cytometry. This invention uses any of various methods of conveyance of the cells through the passage. Included among these methods are centrifugal force and electromotive force, used either individually or together. The invention also uses centrifugal force to urge the cells against one wall of the passage in a single file or a monolayer. Components of the system can also place cells at selected time intervals at a site where each cell is exposed to a source of activation energy. The term "activation energy" is used herein to denote energy directed toward a cell for the purpose of either detection, characterization, or transfection, or two or more such purposes simultaneously. Prime examples of activation energy in accordance with this invention are light energy and electrical energy, and the source of activation energy can thus be a laser beam or and an arrangement of electrodes to produce an electric field, respectively. Sites where the activation energy is directed or focused are referred to herein as "exposure zones," and the term "cell" is used herein to denote any of the various membrane-encased structures that can be detected, analyzed, or treated at the exposure zone. An exposure zone in accordance with this invention is either fixed, i.e., not rotating with the disk, or not fixed, i.e., rotating with the disk, but in all cases, the exposure zone will be at a fixed radial distance from the center of the disk.

In embodiments of the invention in which individual cells are temporarily immobilized at an exposure zone, a preferred means of immobilizing a cell is electrostatic attraction. The electrical force in this case can be an electroosmotic effect in the buffer solution in which the cells are suspended, achieved by constructing the disk from a material that induces the formation of an electrical double layer in the buffer solution adjacent to the surface of the passage wall. An electroosmotic effect can also serve as the conveying means for moving the cells through the passage, as can an electrophoretic effect directly on the cells themselves. Both electroosmotic effects and electrophoretic effects can be induced by electrodes at the ends of the passage. In certain embodiments, the invention provides further control over coordination or synchronization of the cell movement into the exposure zone with the application of the actuation energy at the exposure zone. Where the activation energy is supplied by a laser beam or electroporation electrodes, the actuation of these components can thus be coordinated with the cell movement. This further control is achieved by immobilizing electrodes that when energized create the electrostatic attraction referred to above to halt the travel of a cell by attracting surface charges on the cell. When held by these immobilizing electrodes and rotated into the exposure zone, a cell is exposed to the light beam or electric field, typically in the form of light pulses or voltage pulses. The immobilizing electrodes are then de-energized to release the cell and thereby allow the cell to be replaced by another cell. In certain embodiments as well, cells are conveyed through two or more passages simultaneously and the passages are rotated past the exposure zone in a coordinated manner so that the rate at which the cells are detected or treated in the exposure zone is not limited by the flow rate of the cells through any single passage, even if the cells are conveyed through each passage in a single-file manner.

DESCRIPTION OF THE PREFERRED EMBODIMENTS

Figure 1:
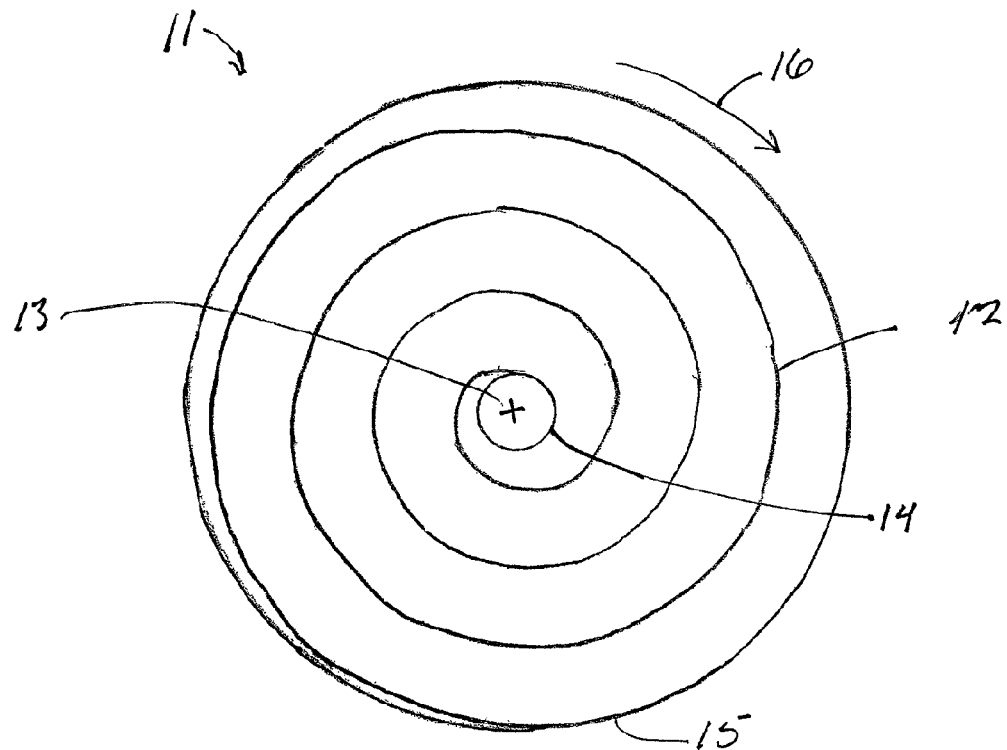
FIG. 1 is a top view of one example of a disk for use in accordance with the present invention.

While the invention is capable of implementation in a wide variety of structures and configurations, an understanding of the invention as a whole will be gained by a detailed review of specific embodiments. Two such embodiments are illustrated in the drawings.

Figure 2:
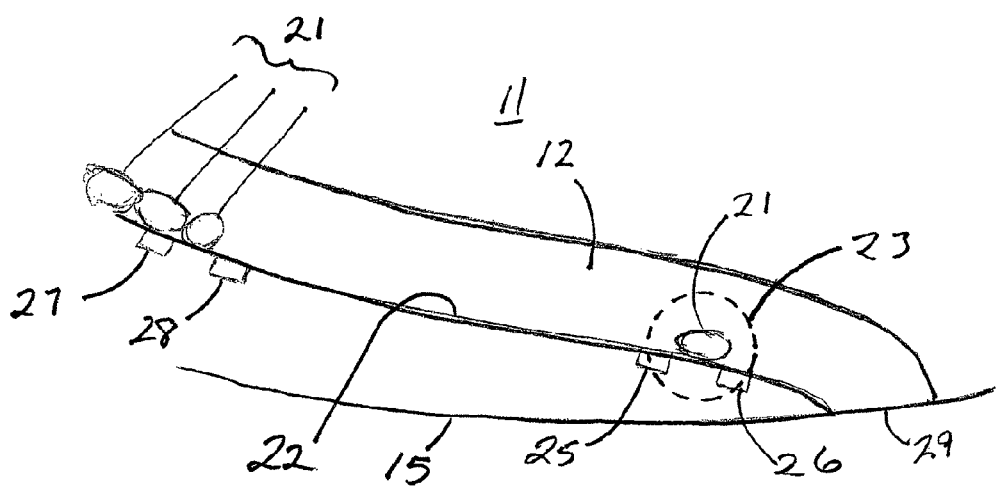
FIG. 2 is an enlarged view of one edge of the disk of FIG. 1.
Figure 3:
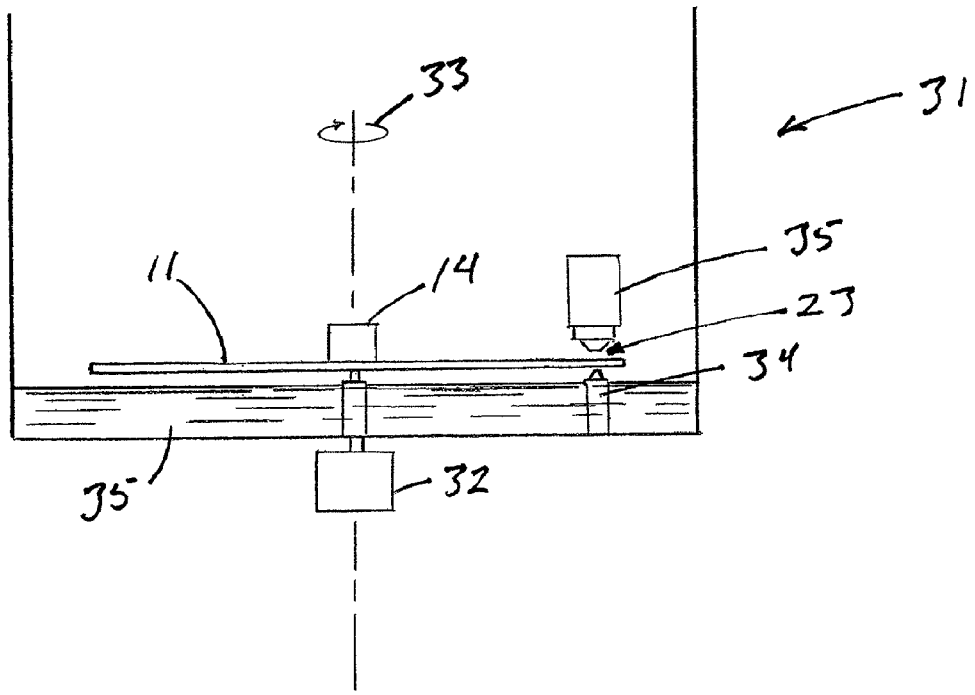
FIG. 3 is a transverse cross section of the disk of FIG. 1 mounted inside a vessel that includes a rotary motor for rotation of the disk plus a source of activation energy.

In the apparatus shown in FIGS. 1, 2 and 3, the passage through which the cells travel is contained in a disk 11, shown in a top view in FIG. 1, and the passage 12 itself forms a spiral in the disk. The passage is either a planar groove (open at the top surface of the disk) or a closed channel (such as a tunnel within the body of the disk) defined by the path within the plane of the disk of a point moving around the center 13 of the disk while continuously receding from the center. (For a disk with a closed channel, FIG. 1 is a cross section parallel to the plane of the disk). At the center of the disk is a reservoir 14 for holding a suspension of the cells, and the spiral passage 12 extends from the reservoir 14 to the outer edge 15 of the disk. As the disk rotates in the direction indicated by the arrow 16, the centrifugal force created by the rotation causes the cells in the spiral passage 12 to travel continuously outward from the center 13. Upon reaching the outer edge 15 of the disk, the cells leave the disk.

An enlarged view of the peripheral region of the disk 11 is presented in FIG. 2. The spiral passage 12 is substantially wider than the cells 21 so that the cells will travel freely through the passage 12, while the centrifugal force urges the cells against the outer wall 22 of the channel where the cells form a single file. Preferably, the width of the channel in the direction perpendicular to the plane of the figure is sufficiently narrow that the cells will form a single file and yet be able to move freely with essentially no resistance from the channel wall except at sites where individual cells are intentionally (and temporarily) held immobile, as described below.

The exposure zone 23, indicated by a circle delineated by a dashed line, is a fixed zone in this embodiment of the invention, i.e., the exposure zone does not rotate as the disk rotates. Each cell enters this zone in succession, and once in the zone, a cell is exposed to a laser beam or a focused electric field, generally in pulse-wise manner, for flow cytometry-type detection or electro or laser-induced poration. To synchronize the position of a cell 21 with the timing of the optical or electrical components at the exposure zone 23, the disk includes a pair of electrodes 25, 26 embedded in the wall of the spiral passage 12. These electrodes 25, 26 are sized and spaced to define a cell holding site between them for retaining a single cell by electrostatic attraction when the electrodes are energized at a polarity opposite to that of the electrical charges on the cell surface. The holding site rotates with the cell and intersects with the exposure zone 23 as the disk rotates. The electrodes 25, 26 remain activated until the cell has been exposed to the activation energy, i.e., the optical or electrical pulses directed to the exposure zone. The electrodes 25, 26 are then deactivated, releasing the cell for completion of its travel through, and ejection from, the passage 12 at the opening 29 at the disk edge. To further ensure that only one cell will enter the exposure zone 23 at a time, the disk can contain additional electrodes 27, 28 embedded in the wall of the spiral passage at a location upstream of the electrodes 25, 26 that will align the cell with the exposure zone. These upstream electrodes 27, 28 can be energized in the same manner as the downstream electrodes 25, 26 to stop the movement of the cells through the passage 12 and thereby to spatially separate these cells from the one cell that is held by the downstream electrodes 25, 26.

Synchronization of the position of the cell at the downstream electrodes 25, 26 with the actuation of the optical or electrical components at the exposure zone 23 can be accomplished in a variety of ways. One is by simple control over the rotation rate of the disk together with knowledge of the speed at which the cells move through the spiral passage at a given rotation rate. Synchronization can also be accomplished by an independent detector such as those commonly used in flow cytometry to indicate the presence of a cell in the exposure zone. A further means of synchronization is the use of an encoded disk which allows the rotational position of the disk to be detected by an appropriate detector. In all of these designs, rotation of the disk can be performed either continuously or in a stepwise manner.

While the disk of FIG. 1 contains a single spiral passage 12, an alternative design is a disk with two or more spiral passages, running parallel to each other. The use of two or more passages with a single exposure zone and a single set of optical or electrical components at the exposure zone allows two or more cells to be detected or treated with a single rotation of the disk. Another variation is the inclusion of two or more exposure zones, equal to the number of spiral passages. Detections and/or treatments of two or more cells can thus be performed simultaneously.

FIG. 3 is a side view of an apparatus that includes the disk 11 of FIGS. 1 and 2 as well as components for rotating of the disk and for detection or treatment of the cells in the exposure zone 23. The apparatus includes a vessel 31 in whose interior is mounted the disk 11 on a rotating pedestal. The rotation of the pedestal and disk is driven by a motor 32 which in this case is external to the vessel. The rotation of the disk is indicated by the arrow 33. The detection or treatment elements that define the exposure zone 23 are represented in this Figure by optical components, including a laser 34 and a microscope/detector 35. These optical components are stationary relative to the vessel and remain so as the disk 11 rotates. The exposure zone 23 is thus the intersection between the laser beam and the disk. The disk 11, or at least the portion of the disk that aligns with the exposure zone 23, is transparent in this embodiment to allow contact of the laser beam with the cell.

The cells upon ejection from the disk 11 are discharged into a buffer solution 35 that covers the floor of the vessel 31. The tip of the laser 34 protrudes above the surface of the buffer solution.

Release of the cells from the reservoir 14 into the spiral passage 12 at a controlled rate can be achieved in a variety of ways. One way is by the same centrifugal force achieved by rotation of the reservoir along with the rotation of the disk. Another is by gravity feed with a flow restriction, by placing the reservoir on the upper surface of the disk as shown and allowing the cells to pass through a port at the bottom for the cell that is small enough to allow only a single cell at a time to pass. Gravity flow can also be promoted by use of a reservoir shaped as a funnel.

Figure 4:
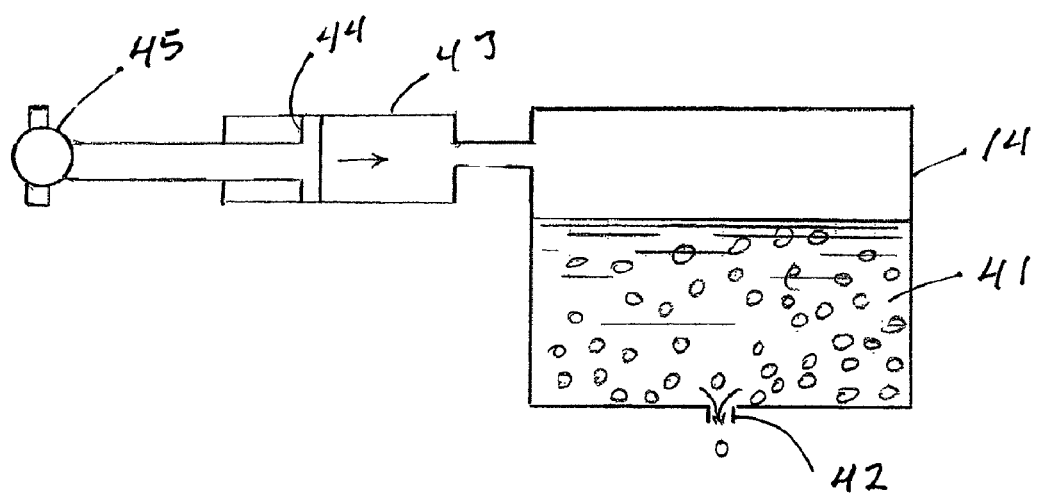
FIG. 4 is a cross section view of the cell reservoir of the preceding Figures.

An example of a reservoir 14 with a mechanism for controlled delivery of the cells is illustrated in FIG. 4. In this Figure, the reservoir 14 is a closed vessel containing a liquid suspension 41 of the cells, with an aperture 42 in the floor of the reservoir. The space above the liquid surface is occupied by air and is pressurized by a syringe 43 with a motorized plunger 44. A stepper motor 45 with a central shaft can serve as the plunger motor. Alternatives to a motorized syringe include piezoelectric diaphragms, vibrating diaphragms, and rotating impellers. The incorporation of these and other alternatives and their adaptation for use in the apparatus will be readily apparent to those of skill in the art.

Figure 5:
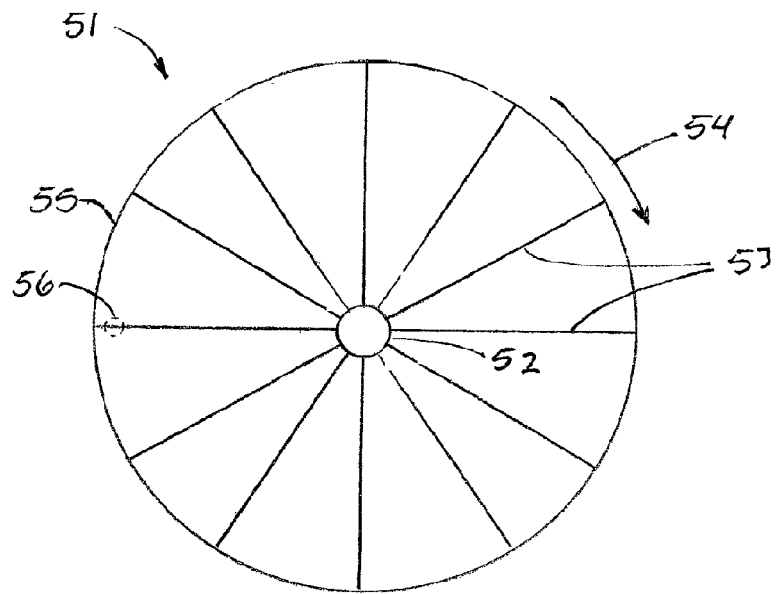
FIG. 5 is a top view of a second example of a disk in accordance with the present invention.

A device that does not involve the use of a spiral channel but is still within the scope of the invention is represented by FIG. 5. The disk 51 in this device contains a central reservoir 52 and radial channels 53 rather than spiral channels. The disk rotates, as indicated by the arrow 54, causing cells that have entered the channels to travel outward toward the outer edge 55 of the disk by centrifugal force. With its straight radial channels, the disk will allow relatively viscous cell suspensions to travel more easily than will the spiral channel of the disk of FIG. 1. The disk rotates past a stationary exposure zone 56 indicated by a circle formed of a dashed line near the outer edge 55 of the disk. With multiple radial channels 53 as shown, the disk allows a number of cells equal to the number of channels to be held at the disk periphery at the same time, and all cells at these locations can be exposed in a single rotation of the disk as they pass the exposure zone 56 in succession. Synchronization of the rotation of the disk with the operation of the exposure zone is achieved in the same manner as the synchronization described above in connection with FIGS. 1 through 4.

Figure 6:
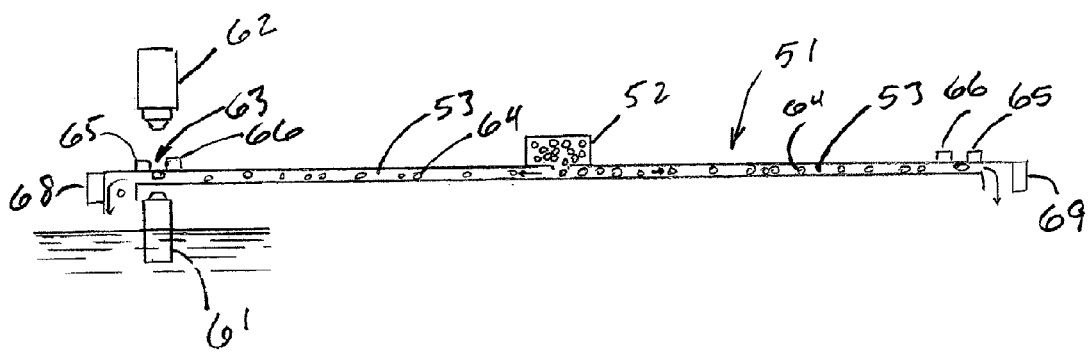
FIG. 6 is a transverse cross section of the disk of FIG. 5.

FIG. 6 is a cross section of the disk 51 along a radius in combination with optical components 61, 62 representing the exposure site. The optical components 61, 62 are the same as those described above in connection with FIG. 3 and the exposure zone 63 is defined by the path of the laser beam between the optical components, again as in FIG. 3. The cells 64 travel radially from the reservoir 52 toward the outer edge of the disk, and are held at the exposure zone 63 by electrodes 65, 66 that are positioned and spaced from each other with the same considerations as the downstream electrodes 25, 26 of FIG. 2. A set of electrodes 65, 66 is included in each of the channels. While a single set of optical components 61, 62 for each of the two visible radial channels is shown, and a single exposure zone 63 is included for the entire device, the device can also include a separate set of optical components for each of the radial channels, permitting exposure of cells in all channels to occur simultaneously. Although not shown in the Figure, each channel 53 can optionally contain an upstream electrode or pair of electrodes analogous to the upstream electrodes 27, 28 of the structure shown in FIG. 2 and serving the same purpose. In both cases, the upstream electrodes can be programmed to become uncharged and re-charged in succession at intervals that will release one cell at a time so that only one cell at a time enters the exposure zone 63.

An electromotive driving force can be used either in conjunction with or in place of the centrifugal force for driving the cells through the radial channels. The electromotive force can be achieved by electrodes 68, 69 at the outer ends of the channels energized at polarities opposite to the surface charges on the cells.

The rotation of the disk 51 in the apparatus of FIGS. 5 and 6 will itself urge the cells against one side of the channel 53, i.e., the side away from the direction of rotation, and if the cells are released from the reservoir 52 slowly enough, this will result in a single file of cells along that side of the wall. Further limitation of the cells to a single file as they approach the exposure zone can be achieved by the holding electrodes 65, 66 which will likewise urge cells within their field of influence against the wall in which they are embedded. While the holding electrodes 65, 66 in FIG. 6 are shown on the upper surface of the disk, the single-file alignment can be achieved by placing the electrodes within the plane of the radial passages and immediately to one side of each passage, rather than above or below the passage.

In the claim or claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. Apparatus for exposing a plurality of single cells in succession to a source of activation energy, said apparatus comprising:
    a disk with a channel formed therein, an outer edge, and a reservoir at the center of said disk capable of retaining a suspension of said cells, said channel commencing at said reservoir and terminating at an outlet port at or adjacent to said outer edge and defining a path of travel whose radial distance from said reservoir continuously increases along said channel;
    means for rotating said disk in a direction that promotes movement of cells through said channel from said central reservoir toward said outlet port;
    means for conveying said cells from said reservoir through said channel toward said outlet port; and
    means for focusing activation energy from said source of activation energy on a portion of said disk as said disk is rotating, said portion defined as an exposure zone and positioned at a fixed radial distance from said reservoir such that said cells pass through said exposure zone in a single-file manner during their passage through said channel.

2. The apparatus of claim 1 wherein said channel is a radial channel.

3. The apparatus of claim 1 wherein said channel is a spiral channel.

4. The apparatus of claim 1 wherein said exposure zone is fixed such that said exposure zone remains stationary as said disk rotates.

5. The apparatus of claim 1 wherein said means for conveying said cells comprises means for imposing an electromotive force through said channel.

6. The apparatus of claim 1 wherein said means for conveying said cells consists of said means for rotating said disk.

7. The apparatus of claim 1 wherein said source of activation energy is a means for imposing an electric field across said exposure zone.

8. The apparatus of claim 1 wherein said source of activation energy is a light beam.

9. The apparatus of claim 1 further comprising means for immobilizing a single cell at a cell holding site within said channel that intersects with said exposure zone as said disk rotates.

10. The apparatus of claim 9 wherein said means for immobilizing a single cell comprises a pair of electrodes in a wall of said channel adjacent to said holding site.

11. The apparatus of claim 1 further comprising an activation site within said channel that intersects with said exposure zone as said disk rotates, said apparatus further comprising means for limiting passage of said cells through said channel such that cells pass through said activation site singly and in succession at preselected intervals.

12. The apparatus of claim 11 wherein said means for limiting passage of said cells through said channel comprises an electrode in a wall of said channel at a cell accumulation site upstream of said activation site.

* * * * *